US00PP34108P2

(12) United States Plant Patent
Westhoff

(10) Patent No.: US PP34,108 P2
(45) Date of Patent: Apr. 5, 2022

(54) ***DIDELTA* PLANT NAMED 'WESDIFANFISISTI'**

(50) Latin Name: *Didelta hybrida*
Varietal Denomination: Wesdifanfisisti

(71) Applicant: GARTENBAU und SPEZIALKULTUREN WESTHOFF GbR, Sudlohn (DE)

(72) Inventor: Heinrich Westhoff, Sudlohn (DE)

(73) Assignee: GARTENBAU und SPEZIALKULTUREN WESTHOFF GbR, Südlohn (DE)

( * ) Notice: Subject to any disclaimer, the term of this patent is extended or adjusted under 35 U.S.C. 154(b) by 0 days.

(21) Appl. No.: 17/371,383

(22) Filed: Jul. 9, 2021

(51) Int. Cl.
*A01H 5/12* (2018.01)
*A01H 6/14* (2018.01)

(52) U.S. Cl.
USPC ..... Plt./373

(58) Field of Classification Search
USPC ..... Plt./373
CPC ... A01H 5/12; A01H 5/00; A01H 6/00; A01H 6/14
See application file for complete search history.

(56) References Cited

PUBLICATIONS

Upov International Union for the Protection of New Varieties of Plants Explanatory Notes on Variety Denominations Under the Upov Convention, UPOV/ONF/12/5, 2015, cover page and p. 5. (Year: 2015).*

* cited by examiner

*Primary Examiner* — June Hwu
(74) *Attorney, Agent, or Firm* — C. Anne Whealy

(57) ABSTRACT

A new and distinct cultivar of *Didelta* plant named 'Wesdifanfisisti', characterized by its semi-succulent potted plant that is outwardly spreading, low-growing and mounded to semi-trailing plant habit; vigorous growth habit; freely branching habit; dense and bushy appearance; silvery green-colored stems and leaves; and relative tolerance to high temperatures.

2 Drawing Sheets

Figure 1:
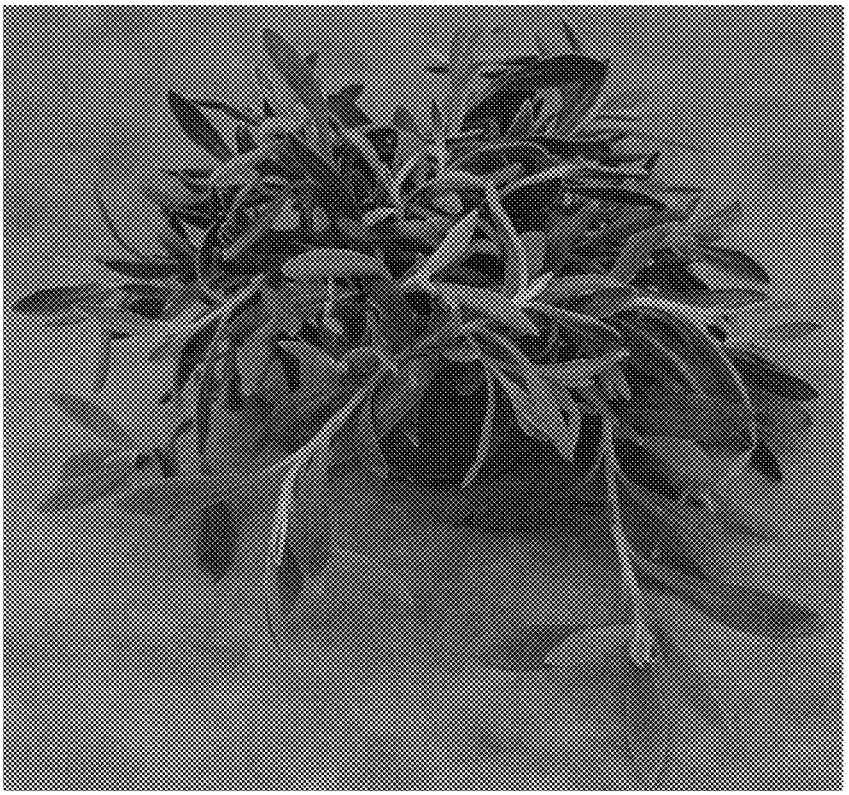

Botanical designation: *Didelta hybrida.*
Cultivar denomination: 'WESDIFANFISISTI'.

STATEMENT REGARDING PRIOR DISCLOSURES BY INVENTOR/APPLICANT & ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or the Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Didelta* plant, botanically known as *Didelta hybrida* and hereinafter referred to by the name 'Wesdifanfisisti'.

The new *Didelta* plant is a naturally-occurring whole plant mutation of *Didelta hybrida* 'Wesdifanfisist', not patented. The new *Didelta* plant was discovered and selected by the Inventor as a single plant from within a population of plants of 'Wesdifanfisist' controlled greenhouse environment in Südlohn, Germany in May, 2020.

Asexual reproduction of the new *Didelta* plant by terminal vegetative cuttings in a controlled environment in Südlohn, Germany since June, 2020, has shown that the unique features of this new *Didelta* plant are stable and reproduced true to type in successive generations.

SUMMARY OF THE INVENTION

Plants of the new *Didelta* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Wesdifanfisisti'. These characteristics in combination distinguish 'Wesdifanfisisti' as a new and distinct *Didelta* plant:

1. Semi-succulent potted plant that is outwardly spreading, low-growing and mounded to semi-trailing plant habit.
2. Vigorous growth habit.
3. Freely branching habit; dense and bushy appearance.
4. Silvery green-colored stems and leaves.
5. Relatively tolerant to high temperatures.

Plants of the new *Didelta* differ primarily from plants of the mutation parent, 'Wesdifanfisist' in the following characteristics:

1. Plants of the new *Didelta* are more trailing than and not as upright as plants of 'Wesdifanfisist'.

2. Plants of the new *Didelta* are larger and more vigorous than plants of 'Wesdifanfisist'.
3. Plants of the new *Didelta* are more freely branching than plants of 'Wesdifanfisist'.
4. Plants of the new *Didelta* have larger leaves than plants of 'Wesdifanfisist'.
5. Plants of the new *Didelta* are more tolerant to high temperatures than plants of 'Wesdifanfisist'.

Plants of the new *Didelta* can be compared to plants of unnamed selections of *Didelta hybrida*, not patented. In side-by-side comparisons, plants of the new *Didelta* differ primarily from plants of unnamed selections of *Didelta hybrida* in the following characteristics:

1. Plants of the new *Didelta* are more trailing than and not as upright as plants of unnamed selections of *Didelta hybrida.*
2. Plants of the new *Didelta* are more vigorous than plants of unnamed selections of *Didelta hybrida.*

BRIEF DESCRIPTION OF THE PHOTOGRAPHS

The accompanying colored photographs illustrate the overall appearance of the new *Didelta* plant showing the colors as true as it is reasonably possible to obtain in colored reproductions of this type. Colors in the photographs may differ slightly from the color values cited in the detailed botanical description which accurately describe the colors of the new *Didelta* plant.

The photograph on the first sheet (FIG. 1) is a side perspective view of a typical plant of 'Wesdifanfisisti' grown in a container.

Figure 2:
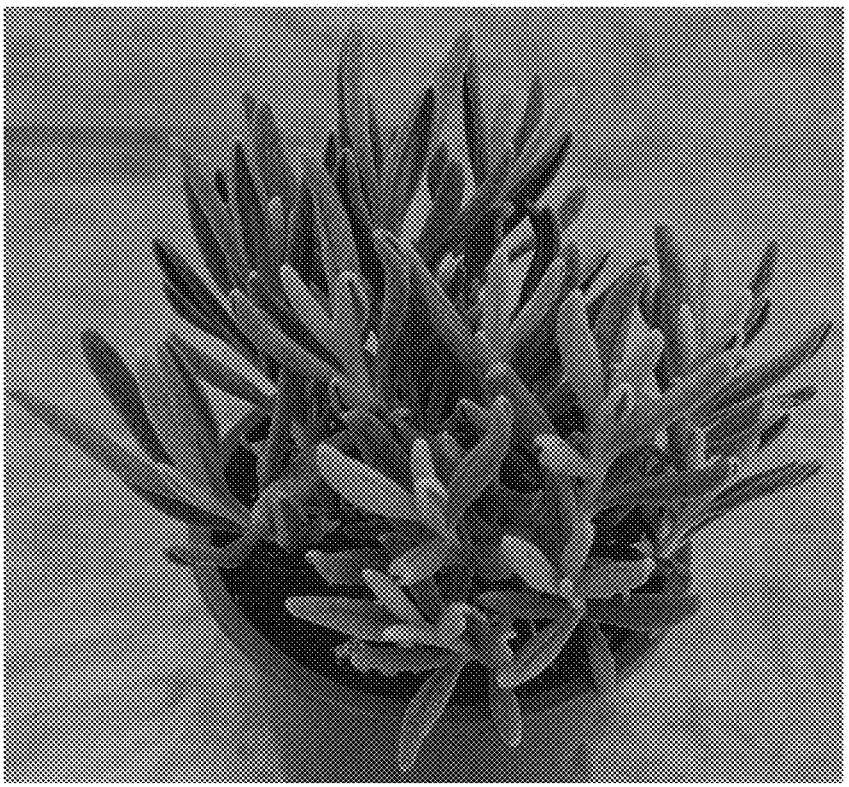

The photograph on the second sheet (FIG. 2) is a side perspective view of a typical plant of the mutation parent, 'Wesdifanfisit'.

DETAILED BOTANICAL DESCRIPTION

The aforementioned photographs and following observations and measurements describe plants grown in 12-cm containers during the spring in a glass-covered greenhouse in Südlohn, Germany and under cultural practices typical of commercial *Didelta* production. During the production of the plants, day temperatures ranged from 18° C. to 22° C., night temperatures ranged from 16° C. to 18° C. and light levels ranged from 3,000 to 50,000 lux. Plants were pinched one time and were 14 weeks old when the photographs and description were taken. In the following description, color references are made to The Royal Horticultural Society Colour Chart, 2001 Edition, except where general terms of ordinary dictionary significance are used.

Botanical classification: *Didelta hybrida* 'Wesdifanfisisti'.

Parentage: Naturally-occurring whole plant mutation of *Didelta hybrida* 'Wesdifanfisist', not patented.

Propagation:

*Type*.—By terminal vegetative cuttings.

*Time to initiate roots, summer*.—About 21 to 24 days at temperatures about 18° C. to 20° C.

*Time to initiate roots, winter*.—About 24 to 28 days at temperatures about 18° C. to 20° C.

*Time to produce a rooted young plant, summer*.—About three to four weeks at temperatures about about 18° C. to 20° C.

*Time to produce a rooted young plant, winter*.—About four to five weeks at temperatures about 18° C. to 20° C.

*Root description*.—Medium in thickness, fibrous; close to 158A in color, actual color of the roots is dependent on substrate composition, water quality, fertilizer type and formulation, substrate temperature and physiological age of roots.

*Rooting habit*.—Freely branching; medium density to dense.

Plant description:

*Plant and growth habit*.—Semi-succulent potted plant that is outwardly spreading, low-growing and mounded to semi-trailing plant habit; vigorous growth habit and rapid growth rate; freely branching habit with lateral branches potentially developing at every node; dense and bushy appearance.

*Plant height*.—About 12 cm to 15 cm.

*Plant diameter*.—About 30 cm.

Lateral branch description:

*Length*.—About 10 cm to 13 cm.

*Diameter*.—About 2 mm to 4.5 mm.

*Internode length*.—About 2 cm.

*Strength*.—Strong; flexible.

*Texture and luster*.—Densely pubescent.

*Color, developing and developed*.—Close to 193C.

Leaf description:

*Arrangement*.—Alternate, simple; sessile.

*Length*.—About 5 cm to 7 cm.

*Width*.—About 1.4 cm.

*Shape*.—Oblanceolate.

*Apex*.—Acute to obtuse.

*Base*.—Attenuate.

*Margin*.—Entire.

*Texture and luster, upper and lower surfaces*.—Densely and finely pubescent, lanate; matte.

*Venation pattern*.—Pinnate.

*Color*.—Developing leaves, upper surface: Close to 192C. Developing leaves, lower surface: Close to 194B. Fully expanded leaves, upper surface: Close to 146C; venation, close to 146D. Fully expanded leaves, lower surface: Close to 147C; venation, close to 147D.

Flower description: To date, plants of the new *Didelta* have not been observed to develop flowers.

Pathogen resistance: To date, plants of the new *Didelta* have not been observed to be resistant to pathogens common to *Didelta* plants.

Garden performance: Plants of the new *Didelta* have been observed to have good garden performance and to tolerate temperatures ranging from about 5° C. to about 34° C.

It is claimed:

1. A new and distinct *Didelta* plant named 'Wesdifanfisisti' as illustrated and described.

* * * * *